United States Patent
Prisco

(10) Patent No.: US 7,287,856 B2
(45) Date of Patent: Oct. 30, 2007

(54) HYPOALLERGENIC DISPOSABLE TIP COVER FOR TONOMETRY APPARATUS

(75) Inventor: John R. Prisco, Jacksonville, FL (US)

(73) Assignee: Reichert, Inc., Depew, NY (US)

( * ) Notice: Subject to any disclaimer, the term of this patent is extended or adjusted under 35 U.S.C. 154(b) by 526 days.

(21) Appl. No.: 10/923,312

(22) Filed: Aug. 20, 2004

(65) Prior Publication Data

US 2006/0063997 A1    Mar. 23, 2006

(51) Int. Cl.
- A61B 3/00    (2006.01)
- A61B 3/14    (2006.01)
- A61B 3/16    (2006.01)

(52) U.S. Cl. ............... 351/219; 351/209; 600/406
(58) Field of Classification Search ........ 351/200–223; 600/398–406
See application file for complete search history.

(56) References Cited

U.S. PATENT DOCUMENTS

| | | | | |
|---|---|---|---|---|
| 3,971,746 A | 7/1976 | Hirai et al. | ............... | 524/161 |
| 4,922,914 A | 5/1990 | Segal et al. | ............... | 600/406 |
| 4,951,671 A | 8/1990 | Coan | ............... | 600/405 |
| 5,002,057 A | 3/1991 | Brady | ............... | 600/406 |
| 5,031,622 A | 7/1991 | LaHaye | ............... | 600/398 |
| 5,070,875 A | 12/1991 | Falck et al. | ............... | 600/405 |
| 5,318,029 A | 6/1994 | Palese | ............... | 600/399 |
| 5,343,861 A | 9/1994 | Herman | ............... | 600/406 |
| 5,954,646 A | 9/1999 | Jost et al. | ............... | 600/406 |
| 6,329,444 B1 | 12/2001 | McGlothlin et al. | ............... | 523/105 |
| 2006/0276705 A1* | 12/2006 | Prisco et al. | ............... | 600/406 |

FOREIGN PATENT DOCUMENTS

DE    31 09 716 A1    11/1982

OTHER PUBLICATIONS

PCT Search Report mailed Nov. 11, 2005 (7 pgs).
Brochure entitled "TONO-PEN XL Applanation Tonometer" (7 pgs.); by Medtronic Ophthalmics, A Division of Medtronic USA, Inc. 6743 Southpoint Drive North, Jacksonville, FL 32216-0980 (www.medtronicophthalmics.com).

* cited by examiner

Primary Examiner—M. Hasan
(74) Attorney, Agent, or Firm—Hodgson Russ LLP

(57) ABSTRACT

The invention provides a hypoallergenic disposable cover for the probe tip of a contact tonometer comprising a thin film having an ultimate elongation in the range of 500 to 1000%, a tensile strength in the range of 1000 to 5500 psi and a modulus of elasticity at 100% strain in the range of 50 to 2000 psi, whereby when installed onto the probe tip, the cover creates a barrier against microorganisms from the eye of a patient to said probe tip during a tonometric examination while allowing measurement of intraocular pressure through the disposable tip cover.

15 Claims, 2 Drawing Sheets

HYPOALLERGENIC DISPOSABLE TIP COVER FOR TONOMETRY APPARATUS

THE FIELD OF THE INVENTION

The present invention relates generally to the field of ophthalmological tonometers and more specifically to a hypoallergenic disposable probe tip cover for a contact tonometer, which reduces the possibility of allergic reactions in patients and health care providers while protecting against contamination.

BACKGROUND OF THE INVENTION

A tonometer is an ophthalmological instrument for testing intraocular pressure. Such a test is commonly performed as part of a standard eye examination to detect the early stages of glaucoma. Glaucoma is characterized by an increase in pressure within the eye, which causes visual defects and ultimately may cause blindness. Because the patient seldom experiences any symptoms until major damage occurs, regular testing is essential to detect glaucoma in the early state before the retinal field is seriously diminished, and ocular nerve damage has occurred.

One type of tonometer is a "non-contact" tonometer; one common form of this type of tonometer is known as an "airpuff" tonometer. With this type of tonometer, a gas jet is directed toward the measurement area, which flattens the surface and a measure of reflected incident light yields a relative measurement of intraocular pressure. The non-contact devices are often large, since they include devices for positioning the patient's head, and rely heavily on the skill of the operator for accuracy. Patients sometimes complain of discomfort associated with the blast of air that must be delivered to obtain a measurement.

Another type of tonometer is a "contact" tonometer; one common form of this type is an applanation tonometer. Testing using a contact tonometer involves touching the tip of a probe directly onto the eye surface, and then pressing the tip against the surface toward the eye, thus indenting a portion of the surface of the eye, and determining the amount of force required to produce the given indentation. The resiliency of the surface and the internal pressure of the eyeball resist the flattening or indentation, and such force may be then converted to a measure of intraocular pressure. It is known that contact tonometers give more valid measurements of intraocular pressure, and provide more realizable diagnosis of early stages of glaucoma than the non-contact tonometers. Contact tonometers have been developed which are portable, weigh only a few ounces, and are thus convenient to use in any setting. These devices allow patients using mobility devices, or unable to make an office visit due to mobility, agoraphobia, claustrophobia, bedridden status, etc., to be tested, as the portable contact tonometer may be easily brought to their location. The small size of the instrument also provides a non-threatening glaucoma examination for apprehensive patients.

However, it is also known that a variety of disease pathogens can be found of the surface, and especially in the fluid film that covers the eye. These pathogens include those that related directly to the eye, such as conjunctivitis, and those which are systemic, such as immune system disorders. A disadvantage of contact tonometers is that they must touch the eye, and therefore, may pose a risk of transferring such pathogens from one patient to another, or from patient to health care provider. Various methods have been utilized to reduce the transmission risk, including sterilization of the probe tip between examinations. This method can produce eye irritation, and even damage if the disinfectant is not all removed from the surface. Sterile gloves must be used by the tester, or re-contamination may occur when reinserting the probe. Wiping of the probe tip surface may not be sufficient to remove all pathogens, and may also cause scratching of the probe's surface over time. For these reasons, a more preferred method has been to fit the probes, or contact tips, of contact tonometers with disposable covers, to prevent such transmission. Such covers can be disposed of after each measurement. They also help to protect the eye from injury or irritation. Such covers should be smooth in texture. They must have high mechanical strength so that thin layers may be applied to the probe tip and removed without tearing, and be a non porous barrier to liquids and microorganisms. Such covers are generally formed from materials such as natural latex rubber. However, it has been found that over time, persons can develop allergies to natural latex rubber, including mild contact irritation, delayed hypersensitivity, and systemic allergic reactions caused by antibodies to the proteins in the natural rubber. Persons who work in the health care industry are especially prone to development of such allergies because of multiple repeat exposures to natural latex.

It would be desirable to have a disposable cover formed of a material which would be hypoallergenic compared to natural latex rubber, but which would meet the other requirements of smoothness, strength, resistance to porosity of fluids or microorganisms, and non-irritating to the eye.

It has now been discovered that a hypoallergenic disposable tip cover for a contact tonometer may be formed from synthetic thin film materials such as silicone, polyurethane, polyisoprene and the like and that such cover will provide the required properties while also avoiding allergic reactions in patients and health care providers.

SUMMARY OF THE INVENTION

The invention provides a hypoallergenic disposable probe tip cover for a contact tonometer comprising a thin film material having an ultimate elongation of from about 500% to about 1000%, a tensile strength of from about 1000 to about 5500 psi and a modulus of elasticity at 100% strain of from about 50 to about 2000 psi.

More specifically, the invention provides a hypoallergenic disposable cover for the probe tip of a contact tonometer comprising a thin film having an ultimate elongation of from about 500 to 1000%, a tensile strength of from about 1000 to about 5500 psi and a modulus of elasticity at 100% strain of from about 50 to about 2000 psi, whereby said cover when installed onto said probe tip creates a barrier against microorganisms from the eye of a patient to said probe tip during a tonometric examination while allowing measurement of intraocular pressure through said cover.

In one embodiment, the invention includes a hypoallergenic disposable cover formed from a film selected from the group consisting of polyurethane, polyethylene, polypropylene, polyisoprene, polychloroprene, nitrile, and silicone.

In another embodiment, the invention includes a hypoallergenic disposable cover formed from cis-1,4-polyisoprene.

In another embodiment the hypoallergenic disposable tip cover comprises a ring bead which fits into a groove on the probe of the contact tonometer to hold the tip cover in place.

These terms when used herein have the following meanings.

1. The term "hypoallergenic" means having a decreased tendency to cause an allergic reaction.
2. The term "applanation" means flattening or indentation.
3. The term "tonometer" as used herein, refers to a device for measuring intraocular pressure. The basic principle of a tonometer is that when a pressurized vessel is partly collapsed by an external object the circumferential stresses are removed and the internal and external pressures are equal. This approach has been used to measure intra-ocular pressure, intra-uterine pressure during pregnancy, and to a lesser extent the intraluminal pressure or pulse waveform in some arteries.
4. The term "latex" means an aqueous emulsion of finely divided rubber or plastic particles.
5. The term "synthetic rubber" means a rubbery material which does not contain any natural latex rubber.

All weights, amounts and ratios herein are by weight, unless otherwise specifically noted.

DETAILED DESCRIPTION OF THE PREFERRED EMBODIMENTS

Figure 1:
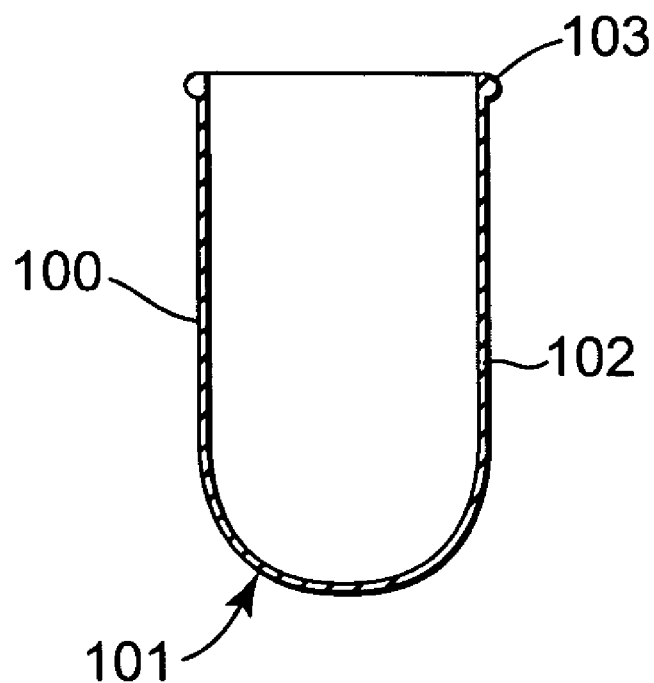
FIG. 1 is a perspective view of a probe cover tip for a contact tonometer apparatus.

The following detailed description describes certain embodiments and is not to be taken in a limiting sense. The scope of the present invention is defined by the appended claims.

The hypoallergenic disposable probe tip cover provided by the invention is a shaped article which is placed over the probe tip of a contact tonometer to shield patients and medical personnel from cross-contamination. The probe tip cover, or sheath, is formed from a hypoallergenic material, and is disposable after a single use. The cover fits over the probe tip of the tonometer and covers at least the measurement area of the probe and is held onto the probe by frictional forces or a combination of frictional forces and retention means.

The hypoallergenic disposable probe tip cover is formed from a "rubbery" material which does not include natural rubber. In other words, the cover is formed from a material which has similar mechanical properties to natural latex rubber without the allergenic properties thereof. Properties which are important include the modulus of elasticity, ultimate elongation and tensile strength. In some embodiments, but not all, optical transparency may be another desirable characteristic. Useful hypoallergenic tip covers typically have a thickness of less than about 0.010 inch, preferably from about 0.0005 inch to about 0.005 inch.

Available synthetic elastomers include but are not limited to nitrile, polyurethanes, polyethylene, polypropylene, polyisoprene, polychloroprene, silicone, styrene-butadiene block copolymers, block copolymers including blocks formed from isoprene, ethylene butylenes, and/or styrene blocks, acrylonitrile-butadiene, polybutadiene and the like. Useful thin films formed from such elastomers are those having an ultimate elongation of from about 500 to 1000%, a tensile strength of from about 1000 to about 5500 psi and a modulus of elasticity at 100% strain of from about 50 to about 2000 psi. In one embodiment, the thin film has a modulus of elasticity is from about 50 to about 500 psi.

In one useful embodiment, the disposable tip covers are formed from synthetic cis-1,4-polyisoprene. Polyisoprene lacks the proteins in natural rubber which can be the basis of allergic reaction. If processed in such a fashion so as not to introduce any irritants such as sulfur or similar proteins to those contained in natural rubber, they are hypoallergenic and have the required properties such as elongation and tensile strength. Polyisoprene polymers and copolymers useful to form probe tip covers of the invention have an elongation of at least about 800%, a tensile strength of at least about 2500 psi, and a modulus of elasticity having a value of from about 250 psi to about 500 psi at 100% strain.

Useful synthetic polyisoprene polymers are available as cis-1,4-polyisoprene from such manufacturers as Goodyear Tire and Rubber Company under the tradename Natsyn™, from Kraton Polymers UK, from Royal Dutch Shell Group, from Nippon Zeon and other suppliers of rubber and elastomeric compounds. The polymer is produced by polymerizing isoprene over a catalyst, under procedures known in the compounding art.

The polyisoprene or other desired elastomer is then formed into a latex by methods such as emulsifying a polymer solution and removing the solvent or liquefying the polymer and combining it with an aqueous medium under conditions favorable to emulsification. Any organic solvents should be removed to leave a solvent-free latex. The latex may contain a minor amount of adjuvants such as antioxidants, plasticizers and the like. When such adjuvants are present, they typically comprise less than 0.1 parts per hundred parts of the elastomeric polymer.

Once prepared, the latex may be cured or crosslinked. While sulfur is used in many elastomeric cure processes, the polymer should be cured, without the addition of any sulfur-containing crosslinking agents for this application, e.g., by use of crosslinking agents or electron beam irradiation. Such irradiation will form crosslinks between the polyisoprene chains by free radical crosslinking. A crosslinking agent may be present to reduce the amount of irradiation needed to form the desired level of crosslinking. Such agents include acrylate and diacrylate compounds including but not limited to 1,6-hexanedioldiacrylate, 1,3-butylene glycol diacrylate and the like, ethyl acrylate, hexyl acrylate, and 2-ethylhexyl acrylate. Peroxides such as bezoyl peroxide, 2,5-dimethyl-2,5-di(t-butylperoxy) hexane dicumyl peroxide and the like are also useful crosslinking agents whether used alone or in the presence of irradiation. The desired degree of crosslinking is that which will produce the desired mechanical properties such as tensile strength, and elongation. When crosslinking agents are included, they typically are present in a range of from about 0.1 to about 10 parts by weight per 100 parts of polyisoprene, preferably from about 0.2 parts to about 5 parts.

The probe tip covers of the invention are then formed by conventional film-forming means including molding, extrusion, blowing and casting of films, and lamination.

In one embodiment, polyisoprene tip covers are formed by dip molding in the absence of sulfur containing components. Specifically, a form with an outer surface that has the desired tip cover configuration is dipped in a liquid medium that contains the polymer latex and then is withdrawn, leaving a continuous film of the liquid polymer over the surface of the form. The article is then stripped from the form. The form may be dipped a single time or a series of dips may be made to build up film thickness.

After the dipping is complete, the film is then dried in place on the form. Such drying may be done at room temperature, but for quicker drying is preferably done in an oven having a temperature of from about 50° C. to about 100° C. for a period of several minutes and then cooled. The formed probe tip cover may be subject to an optional post cure step after the drying step. The final probe tip cover is then removed from the form.

In one embodiment, the form for creating the probe tip cover contains an area which is modified or indented to form a thicker portion, often called a "bead" or "ring bead" of the wall section of the probe tip cover. Such a bead is used in combination with a contact tonometer including a groove in the probe. Such groove is located out of the measurement area and provides a means for holding the probe tip cover in place during examination.

After formation of the probe tip cover, removable holding means may be attached to the cover. One holding means is as a cylinder, which is wrapped around the probe tip cover. Such a removable holding means is used by the installer to place the probe tip cover onto the probe tip of the contact tonometer without contacting the sterile cover. The cylinder is then peeled from the cover without contacting the cover itself to maintain its sterile nature. The cylinder may be formed of a fibrous material such as cardboard, which is easy to grasp, and may include perforations to reduce the manual effort required to remove the cylinder from the cover. Alternative removable holding means includes such structures as peel-off flaps, tabs or flanges. If such removable holding means are not desired, the disposable tip cover may be provided e.g., in a rolled form, where it will be rolled down onto the probe tip and handled only by the lower wall area, or retention bead.

Probe tip covers, whether provided with or without retention means, are typically provided in individual sealed containers such as bags, envelopes, trays, cups and the like to insure the sterile nature of the tip is not disturbed, and that tips need not be handled except when ready for use.

DETAILED DESCRIPTION OF THE DRAWINGS

FIG. 1 shows a probe tip cover of the invention, 100, having a tip area 101 and a wall area 102. Such wall area 102 has a retention bead or ring bead 103 circumferentially formed around the open end 104.

Figure 2:
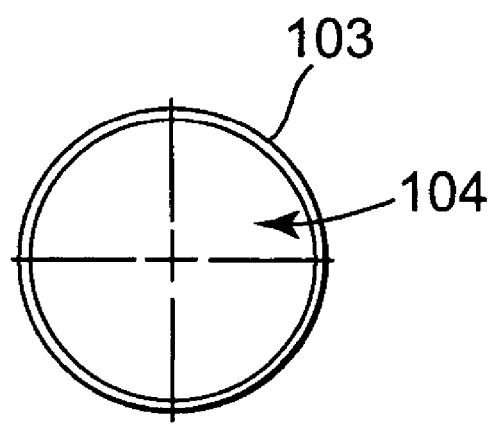
FIG. 2 is a cross-sectional view of a probe tip cover of the invention.

FIG. 2 shows a cross section of the open end 104 of the probe tip cover of the invention including the retention bead 103 circumferentially disposed there around.

Figure 3:
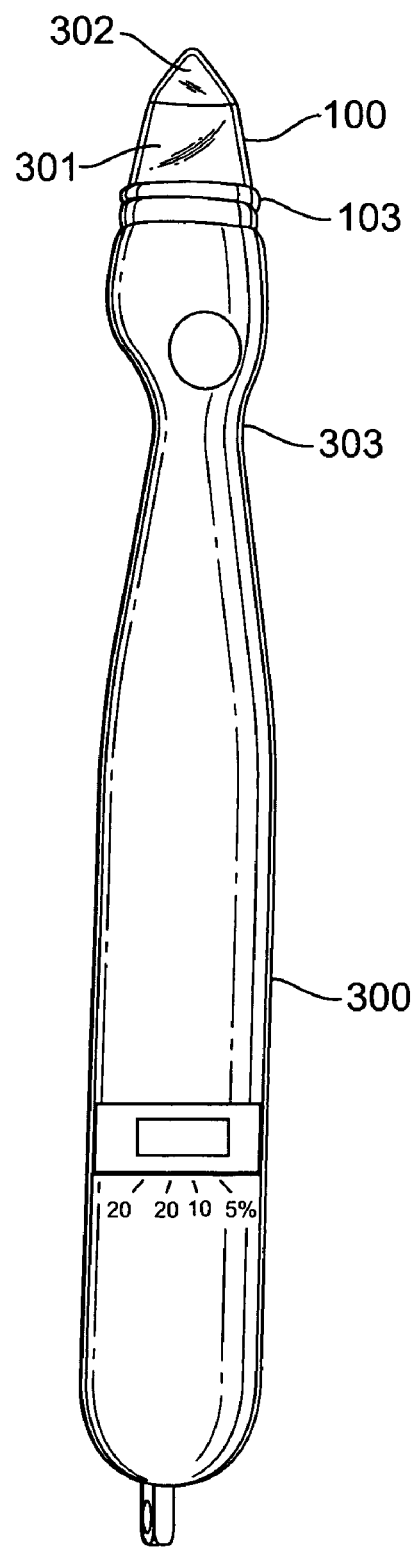
FIG. 3 is a perspective view of a portable contact tonometer apparatus.

FIG. 3 shows a representative contact tonometer 300 having a probe tip 301 having a measurement area 302 with a disposable probe cover 100 disposed over the probe tip 301. The probe cover has a retention bead 103 which holds the probe tip cover 100 onto the probe tip 301. The contact tonometer is held by medical personnel using the grip area 303 and performs the test by contacting the contact area 302 of the probe tip 301 covered by the tip cover 100 to the eye of the patient. The disposable tip cover 100 protects the eye of the patient during the testing procedure.

Although specific embodiments have been illustrated and described herein for purposes of description of the preferred embodiment, it will be appreciated by those of ordinary skill in the art that a wide variety of alternate and/or equivalent implementations calculated to achieve the same purposes may be substituted for the specific embodiments shown and described without departing from the scope of the present invention. Those with skill in the chemical, mechanical, electromechanical, electrical, and computer arts will readily appreciate that the present invention may be implemented in a very wide variety of embodiments. This application is intended to cover any adaptations or variations of the preferred embodiments discussed herein. Therefore, it is manifestly intended that this invention be limited only by the claims and the equivalents thereof.

What is claimed is:

1. A hypoallergenic disposable cover for a probe tip of a contact tonometer, comprising a thin film having an ultimate elongation of from about 500% to about 1000%, a tensile strength of from about 1000 to about 5500 psi and a modulus of elasticity at 100% strain of from about 50 to about 2000 psi, whereby said cover when installed onto said probe tip creates a barrier against microorganisms from the eye of a patient to said probe tip during a tonometric examination while allowing measurement of intraocular pressure through said cover.

2. A hypoallergenic disposable cover for the probe tip of a contact tonometer according to claim 1 wherein said cover has a thickness of from about 0.0005 inch to about 0.010 inch.

3. A hypoallergenic disposable cover for a probe tip of a contact tonometer according to claim 1 wherein said cover has a tubular shape having a wall section with an open end, and a tip section.

4. A hypoallergenic disposable cover for a probe tip of a contact tonometer according to claim 1 wherein said cover tip comprises a material selected from the group consisting of synthetic rubbers.

5. A hypoallergenic disposable cover for a probe tip of a contact tonometer according to claim 1 wherein said cover tip comprises polyisoprene.

6. A hypo allergenic disposable cover for a probe tip of a contact tonometer according to claim 5 wherein said polyisoprene is cis-1,4-polyisoprene.

7. A hypoallergenic disposable cover for the probe tip of a contact tonometer according to claim 1 wherein said cover tip is made by a process selected from the group consisting of film blowing and film casting processes, injection molding, extrusion coating, laminating and dip molding.

8. A hypoallergenic disposable cover for the probe tip of a contact tonometer according to claim 7 wherein said cover tip is made by dip molding.

9. A hypoallergenic disposable cover for the probe tip of a contact tonometer according to claim 1, said tonometer having a transducer measurement diameter wherein said cover includes a tip section for covering said transducer measurement area, said tip section having a diameter of at least about 0.125 inch, and a wall section for securing said cover to said tonometer, said wall section including a retention bead, said ring bead for placement into a groove on said contact tonometer.

10. A hypoallergenic disposable cover for the probe tip of a contact tonometer according to claim 9 wherein said measuring section has a diameter of at least about 0.375 inches.

11. A hypoallergenic disposable cover for the probe tip of a contact tonometer according to claim 9, wherein said cover is provided with a removable holding means for depositing said cover upon said probe tip, said removable holding means enabling an installer to install the disposable cover onto said probe without contact between said installer and said measuring area of said cover.

12. A hypoallergenic disposable cover for the probe tip of a contact tonometer according to claim 11 wherein said removable holding means comprises a cylinder wrapped around said cover.

13. A hypoallergenic disposable cover for the probe tip of a contact tonometer according to claim 11 wherein said cover and said removable holding means are provided inside an individually sealed container.

14. A hypoallergenic disposable cover for a probe tip of a contact tonometer, comprising a thin film formed from a material selected from the group consisting of polyurethane, polyethylene, polypropylene, polyisoprene, polychloroprene, nitrile, and silicone, whereby said cover when installed onto said probe tip creates a barrier against microorganisms from the eye of a patient to said probe tip during a tonometric examination while allowing measurement of intraocular pressure through said cover, said tonometer having a transducer measurement diameter wherein said cover includes a tip section for covering said transducer measurement area, said tip section having a diameter of at least about 0.125 inch, and a wall section for securing said cover to said tonometer, said wall section including a retention bead, said retention bead for placement into a groove on said contact tonometer.

15. A hypoallergenic disposable cover for a probe tip of a contact tonometer, comprising a thin film formed from a material selected from the group consisting of polyurethane, polyethylene, polypropylene, polyisoprene, polychioroprene, nitrile, and silicone, whereby said cover when installed onto said probe tip creates a barrier against microorganisms from the eye of a patient to said probe tip during a tonometric examination while allowing measurement of intraocular pressure through said cover, wherein said cover is provided with a removable holding means for depositing said cover upon said probe tip, said removable holding means enabling an installer to install the disposable cover onto said probe without contact between said installer and said measuring area of said cover, wherein said removable holding means comprises a cylinder wrapped around said cover.

* * * * *